(12) United States Patent
Dellinger

(10) Patent No.: US 10,111,783 B1
(45) Date of Patent: Oct. 30, 2018

(54) SILICA FIBER COMPOSITION AND METHOD OF USE

(71) Applicant: American Nano, LLC, Clemmons, NC (US)

(72) Inventor: Mitch Dellinger, Clemmons, NC (US)

(73) Assignee: American Nano, LLC, Clemmons, NC (US)

(*) Notice: Subject to any disclaimer, the term of this patent is extended or adjusted under 35 U.S.C. 154(b) by 0 days.

(21) Appl. No.: 15/934,599

(22) Filed: Mar. 23, 2018

Related U.S. Application Data

(60) Provisional application No. 62/710,305, filed on Feb. 16, 2018, provisional application No. 62/643,946, filed on Mar. 16, 2018.

(51) Int. Cl.
| | |
|---|---|
| *A61F 13/00* | (2006.01) |
| *C01B 33/157* | (2006.01) |
| *C01B 33/148* | (2006.01) |
| *C01B 33/146* | (2006.01) |
| *C01B 33/158* | (2006.01) |
| *C01B 33/12* | (2006.01) |
| *C07F 7/02* | (2006.01) |
| *D01D 5/00* | (2006.01) |

(52) U.S. Cl.
CPC ...... *A61F 13/00017* (2013.01); *C01B 33/126* (2013.01); *C01B 33/146* (2013.01); *C01B 33/148* (2013.01); *C01B 33/157* (2013.01); *C01B 33/158* (2013.01); *C07F 7/025* (2013.01); *D01D 5/0015* (2013.01); *A61F 2013/00787* (2013.01)

(58) Field of Classification Search
CPC ...... A61F 13/00017; A61F 2013/00787; C07F 7/025; D01D 5/0015; C01B 33/126; C01B 33/14; C01B 33/146; C01B 33/148; C01B 33/157; C01B 33/158
See application file for complete search history.

(56) References Cited

U.S. PATENT DOCUMENTS

| | | |
|---|---|---|
| 8,088,965 B2 | 1/2012 | Thierauf |
| 8,512,741 B2 | 8/2013 | Tan |
| 8,647,557 B2 | 2/2014 | Yeo |
| 9,554,463 B2 | 1/2017 | Sethumadhavan |
| 2012/0244292 A1 | 9/2012 | Lee |

(Continued)

FOREIGN PATENT DOCUMENTS

| | | | |
|---|---|---|---|
| CN | 102652903 A | * | 9/2012 |
| WO | 2017186201 | | 11/2017 |

OTHER PUBLICATIONS

Choi, et al., "Silica Nanofibers From Electrospinning/Sol-Gel Process," Journal of Materials Science Letters 22, 2003, 891-893.

(Continued)

*Primary Examiner* — Anthony J Zimmer
(74) *Attorney, Agent, or Firm* — Morgan, Lewis & Bockius LLP

(57) ABSTRACT

Embodiments of the invention include methods for making silica fiber mats useful for treatment of animal wounds and tissue, as well as for other applications in industry. The fiber mats are formed via electrospinning of a sol gel produced with a silicon alkoxide reagent, such as tetraethyl ortho silicate, alcohol solvent, and an acid catalyst.

29 Claims, 12 Drawing Sheets

(56) References Cited

U.S. PATENT DOCUMENTS

2013/0115186 A1   5/2013   Baecker

OTHER PUBLICATIONS

Geltmeyer, et al., "The Influence of Tetraethoxysilane Sol Preparation on the Electrospinning of Silica Nanofibers," J Sol-Gel Sci Technol (2016) 77:453-462.

Milea et al., The Influence of Parameters in Silica Sol-Gel Process, Bulletin of the Transilvania University of Braș ov Series I: Engineering Sciences • vol. 4 (53) No. 1-2011.

Sakka et al., "The Sol-Gel Transition in the Hydrolysis of Metal Alkoxides in Relation to the Formation of Glass Fibers and Films," Journal of Non-Crystalhne Solids 48 (1982) 31-46.

\* cited by examiner

SILICA FIBER COMPOSITION AND METHOD OF USE

PRIORITY

This Application claims the benefit of U.S. Provisional Application No. 62/710,305 filed Feb. 16, 2018, and U.S. Provisional Application No. 62/643,946 filed Mar. 16, 2018, which are hereby incorporated by reference in their entireties.

BACKGROUND

Wound healing involves a well-coordinated series of biological processes that include both tissue destruction and tissue regeneration. For example, during normal wound healing, neutrophils and monocytes are recruited to the wound during an early inflammatory phase. The neutrophils phagocytize debris and micro-organisms; monocytes and other cells release enzymes in the surrounding matrix to digest damaged tissue. Fibrin is broken down as part of this process, and the degradation products attract fibroblasts and epithelial cells to the site of the wound. Macrophages recruited to the wound (as well as other cells) secrete extracellular enzymes that act on all components of the extracellular matrix and are responsible for removal of devitalized tissue. Macrophages also secrete a variety of cytokines and growth factors that can stimulate keratinocytes, fibroblasts and angiogenesis, which promotes the transition to the proliferative phase of healing. The proliferation phase is characterized by angiogenesis, collagen deposition, granulation tissue formation, wound contraction and epithelialization. Proliferation involves replacement of dermal tissues as well as contraction of the wound.

While destruction of collagen is important during the early phases of wound healing, its deposition and remodeling is critical for later stages. During wound healing, the wound bed fills in from the bottom up with collagen and must be maintained in an optimal environment (appropriate moisture balance and temperature) before the epithelial cells will begin to proliferate and migrate across the wound's surface to close the wound. The collagen structures provide the cells with the needed biological environment for development, organogenesis, cell growth, and wound repair.

Chronic wounds are wounds that have not progressed through this normal, orderly sequence of repair. Further, chronic wounds may eventually pass through the repair process without restoring sustained anatomical and functional tissue. Chronic wounds can result when the body has failed to correct for the causes of the wound, and/or where there is not a conducive environment for healing. For example, newly deposited collagen can be enzymatically destroyed by an uncontrolled inflammatory response, making it difficult for dermal cells to populate the wound and proliferate.

The present invention provides compositions and methods for promoting wound healing, including for acute and chronic wounds, and wounds that result from physical, biological, or genetic causes that interfere with normal wound healing physiology.

SUMMARY OF THE DISCLOSURE

The present invention in various aspects and embodiments provides methods for making silica fiber mats useful for treatment of animal wounds and tissue, as well as for other applications in industry. The methods comprise preparing a sol with a silicon alkoxide reagent, such as tetraethyl ortho silicate (TEOS), alcohol solvent, and an acid catalyst, and transitioning the sol for at least 2 days and less than 7 days under conditions where humidity and temperature are controlled. The sol-gel is electrospun to create a silica fiber mat with superior texture and properties.

In some embodiments, the composition is a lightweight structure composed of silica fiber (e.g., silicon dioxide nanofiber). By ripening ("transitioning") the sol under controlled environmental conditions, and/or monitoring the properties of the sol during the ripening/transitioning process, the relatively short window to successfully electrospin the sol-gel can be identified to prepare a superior composition for wound care and other applications.

In various aspects, the present invention provides compositions and methods for improving integrity of injured tissue in a subject, including for accelerating or improving healing of acute or chronic wounds. The compositions comprise a silica fiber matrix, which is applied to injured tissue to support tissue regeneration and healing. In some embodiments, the silica fiber matrix is a non-biodegradable scaffold that is not removed from the wound (unlike a conventional wound dressing), but becomes integrated with the regenerated tissue.

In accordance with embodiments of the invention, the silica fiber composition, when applied to wounded tissue, acts as a non-biodegradable scaffold that supports tissue healing, regeneration, and/or integrity. The composition acts as a collagen biomimetic at the site of tissue injury, providing an environment conducive for regeneration and growth of, for example, dermal cells.

In various embodiments, the controlled environment for transitioning the sol may involve controlled conditions in terms of humidity, temperature, and optionally barometric pressure. For example, the humidity may be controlled within the range of about 30% to about 90% or from about 40% to about 80%. The temperature may be controlled within the range of from about 50° F. to about 90° F. By controlling the environmental conditions during transitioning, the gel can be electrospun during the time when spinning is optimal, which can occur in a very small window of only several minutes if the ripening process is accelerated by direct heat. When transitioning the sol at a constant humidity in the range of about 50% to 70% and a temperature of about 60 to 80° F., the sol will transition (gelatinize) in a few days, and the window for successful electrospinning can be expanded to at least several hours, and in some embodiments several days. The sol may therefore be transitioned in an enclosure which may include an exhaust fan and one or more environmental monitors, such as a temperature reading device and/or a humidity reading device. Further, gases produced or released by the sol during the transitioning process and/or relative weight of the sol can be monitored to determine the suitable or optimal time for electrospinning.

If the sol-gel is prepared to allow for optimal electrospinning, as described herein, it is possible to electrospin fiber mats having a thickness of at least about ⅛ inch, or at least about ¼ inch, or at least about ⅓ inch, or at least about ½ inch, which are easier to handle for application of fibers to a wound. Indeed, formation of fiber mats of thicknesses in accordance with embodiments of the present invention enables the separation, if necessary or desired, of one or more layers of entangled fibers from a single mat for applications such as wound care.

In some embodiments, the fiber composition is applied to the tissue or wound as a thin layer of fibers, e.g., just enough to cover the wound, followed by repeated application as necessary. In some embodiments, the fiber composition is processed into a fine powder or dust, which is applied to the tissue. In some embodiments, the powder or dust is mixed with a topical composition, such as a lotion, ointment, paste, cream, foam, or gel. In these embodiments, the topical composition may comprise one or more pharmaceutical or antimicrobial agents, such as an antibiotic, an antiseptic, an anti-inflammatory agent, or immunosuppressant.

Application of the composition during the healing process can provide for accelerated healing, of both acute and chronic wounds, and can prevent or reduce tissue scarring. When the topical composition is applied to the skin that has a blemish like acne, cracks in skin, loss of integrity due to age or environmental insult (sun, wind, or cold, etc.), the scaffolding is left behind in the small wound for cells to grow into. This speeds up the healing process and helps to reduce scarring.

In some embodiments, the wound is a first or second degree burn, scrape, or cut, or a minor wound that does not go deeper than the base lamina. In some embodiments, the wound includes damage including or past the base lamina. In some embodiments, the wound is a third degree burn, diabetic ulcer, chronic pressure sore, or gangrenous wound. In some embodiments, fibers are applied once to four times daily to cover the wound. Fibers are generally reapplied when fibers are no longer visible in the wound. An additional wound cover can be employed where necessary, as long as air and oxygen are not restricted from the wound.

In some embodiments, the subject has a genetic blistering disease, such as epidermolysis bullosa. In people born with EB, the two skin layers lack the protein anchors that hold them together, resulting in extremely fragile skin, where even minor mechanical friction like rubbing or pressure will separate the layers of the skin and form blisters and painful sores. In these embodiments, the composition will become integrated with the base lamina, and help anchor the skin. Thus, over time, the skin exhibits improved integrity as sores and blisters are continually treated. Further, the reduction in pain can be important for these patients to perform daily activities, such as bathing or traveling.

Other applications of the fiber composition in industry are described herein.

Other aspects and embodiments will now be described by the following detailed description.

DETAILED DESCRIPTION

Figure 1A:
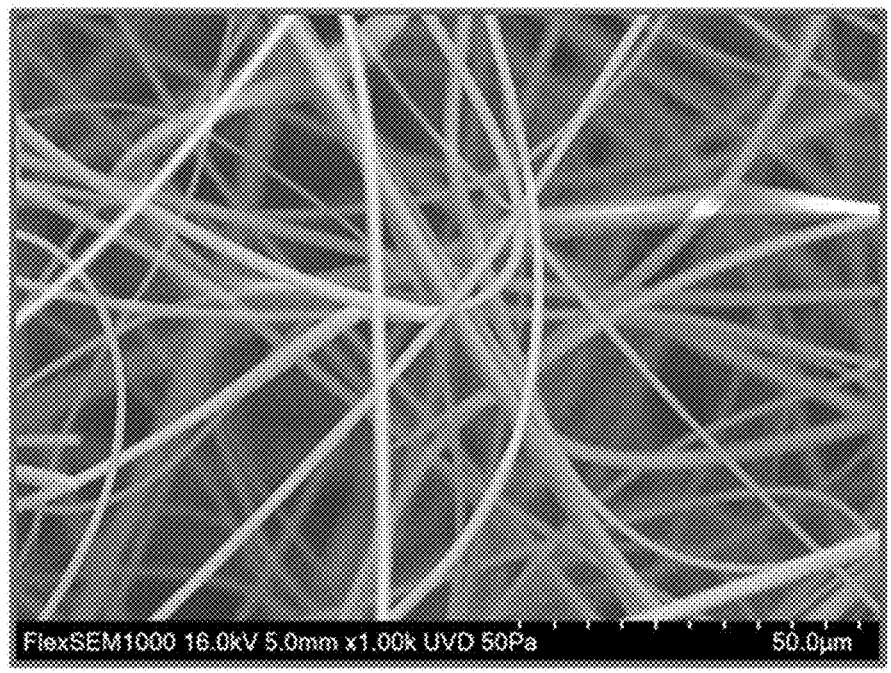
FIGS. 1A-D shows Scanning Electron Microscopy (SEM) images of fibers spun in 10 accordance with this disclosure. Images in FIGS. 1A-D, respectively are at 50, 100, 200, and 500 micron scale. As shown, the fibers are flexible, smooth, dense, and continuous (not fractured).
Figure 1B:
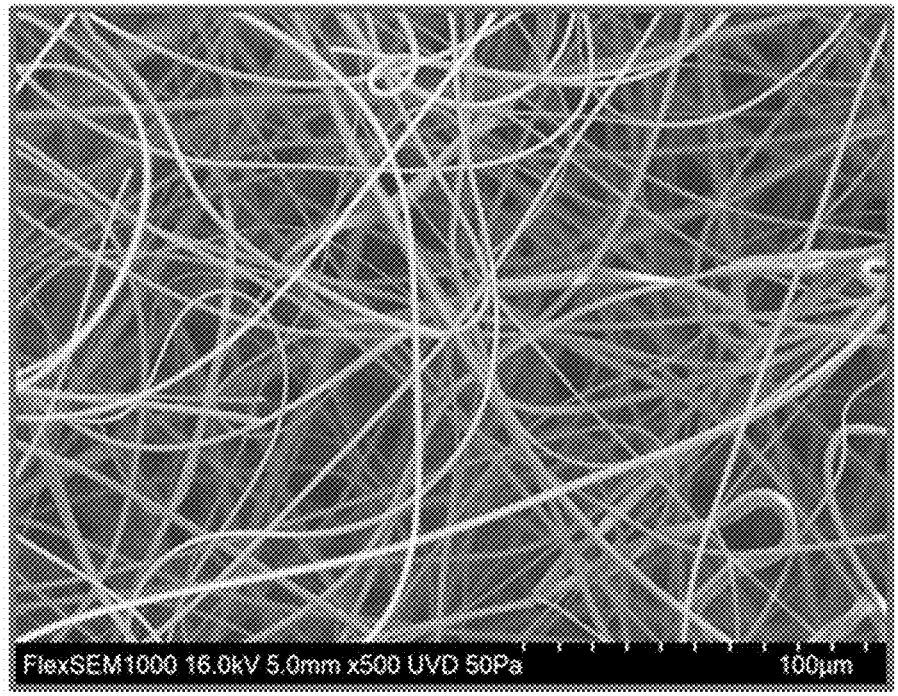
Figure 1C:
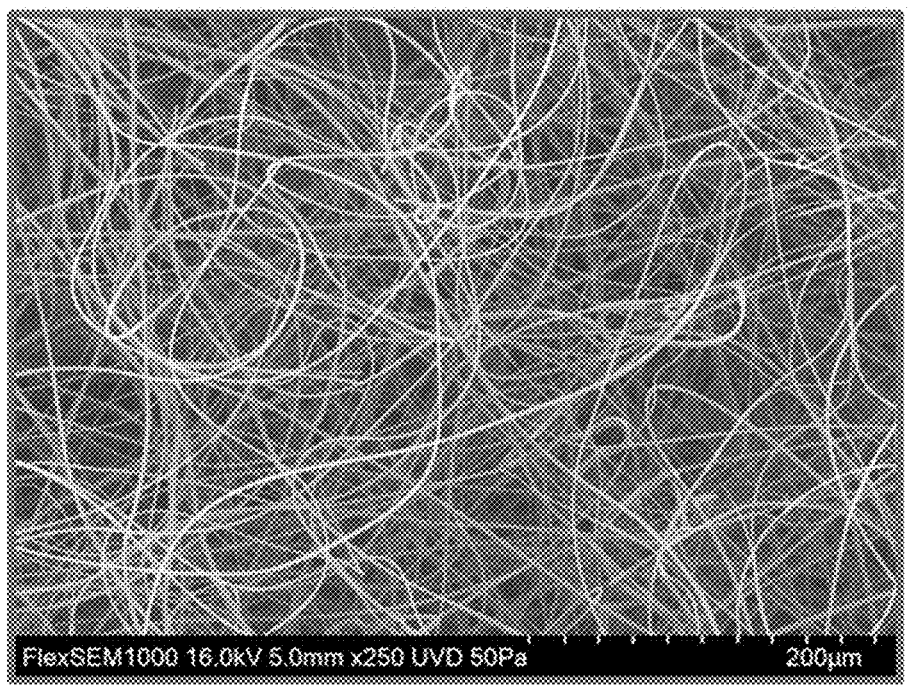
Figure 1D:
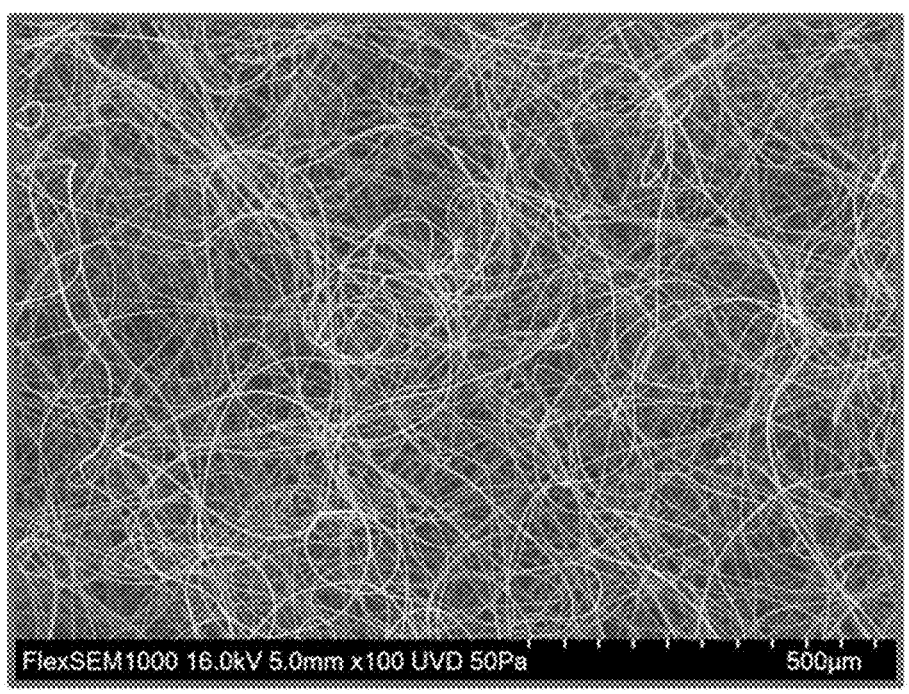
Figure 2A:
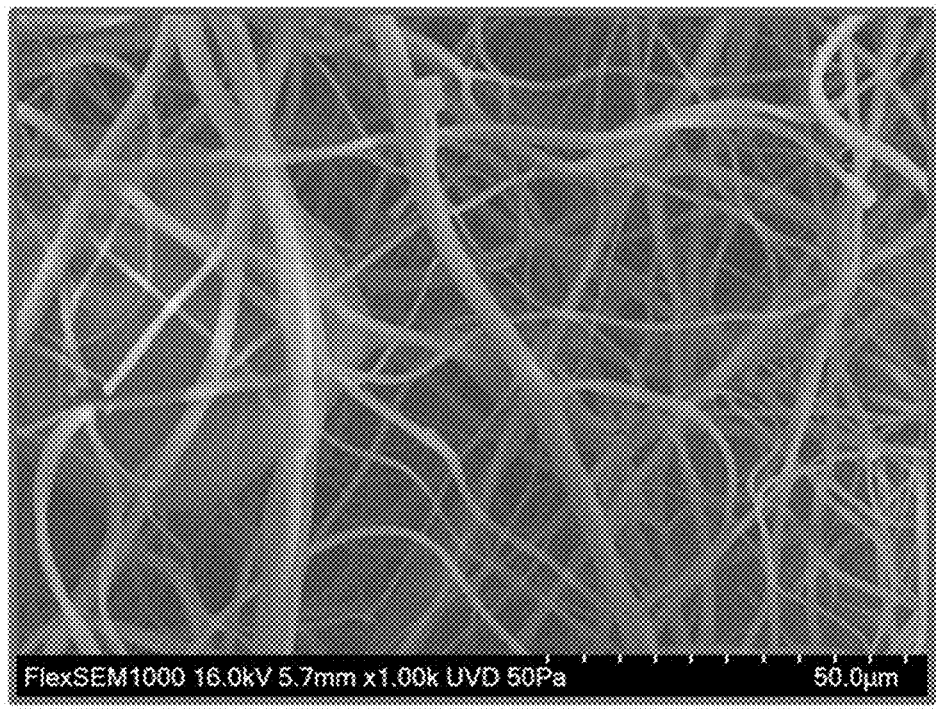
FIGS. 2A-D shows Scanning Electron Microscopy (SEM) images of fibers that were electrospun at a non-optimal time (before the sol-gel was fully ripened). Images in FIGS. 2A-D, respectively are at 50, 100, 200, and 500 micron scale. As shown, the fibers appear rigid, with many fractures visible, and with formation of clumps.
Figure 2B:
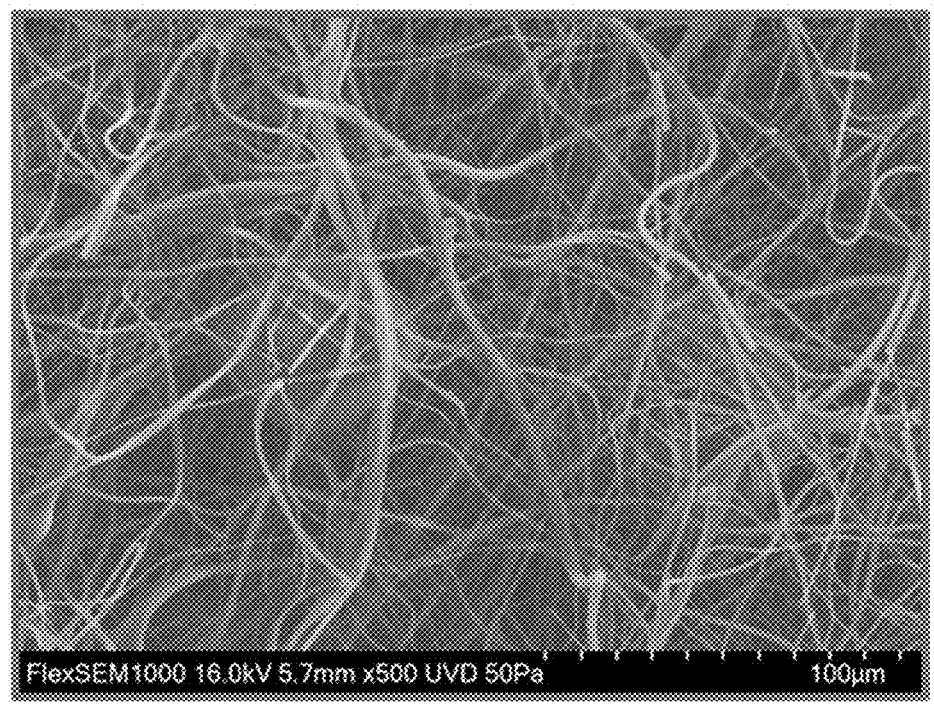
Figure 2C:
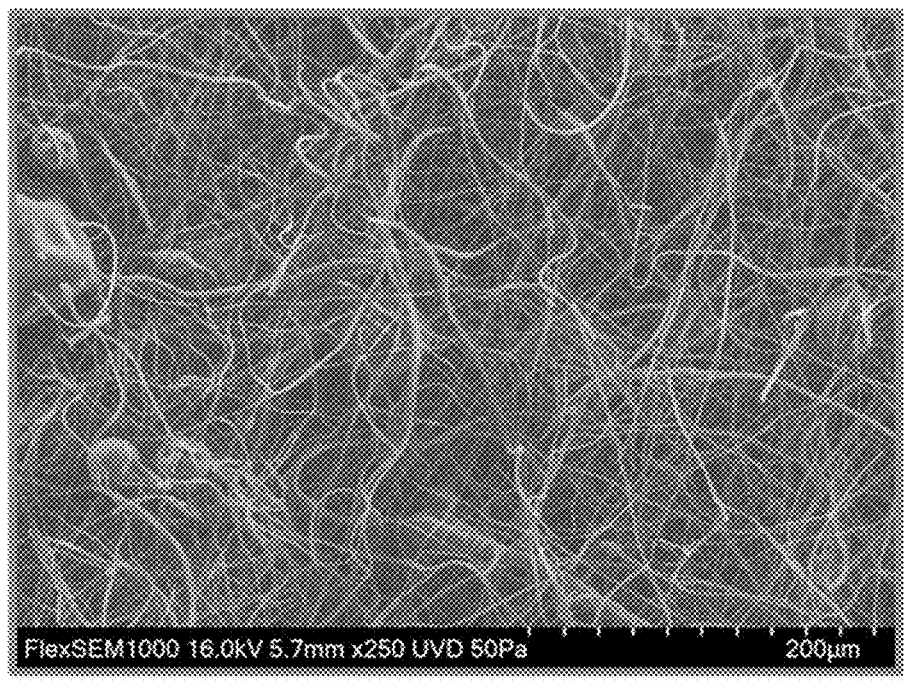
Figure 2D:
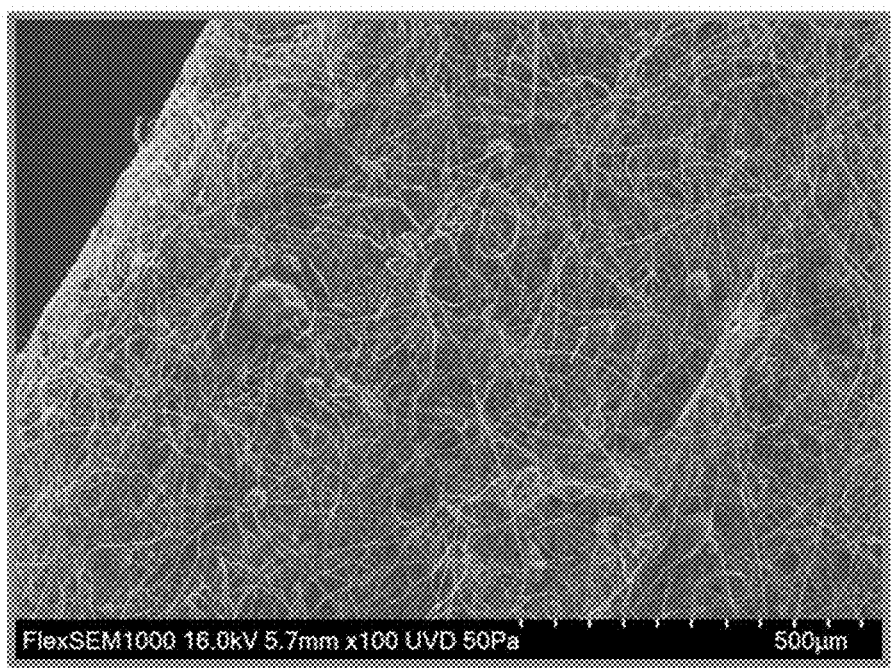

The present invention in various aspects and embodiments provides methods for making silica fiber mats useful for treatment of animal wounds and tissue, as well as other applications in industry. The methods comprise preparing a sol with a silicon alkoxide reagent, such as tetraethyl ortho silicate (TEOS), alcohol solvent, and an acid catalyst, and transitioning the sol for at least 2 days and less than 7 days under conditions where humidity and temperature are controlled. The sol-gel is electrospun to create a silica fiber mat with superior texture and properties.

The present invention provides compositions and methods for improving integrity of injured tissue in a subject, including for accelerating or improving healing of acute or chronic wounds. The compositions comprise a silica fiber matrix, which is applied to injured or inflamed tissue to support tissue regeneration, healing, and/or pain reduction In some embodiments, the composition is a lightweight structure composed of silica fiber (e.g., silicon dioxide nanofiber). The composition is formed from a gelatinous material that is electrospun to form a fiber mat (e.g., a non-woven mat). For example, the composition may be prepared by electrospinning a sol-gel, which can be prepared with a silicon alkoxide reagent, such as tetraethyl ortho silicate (TEOS), alcohol solvent, and an acid catalyst.

Known processes do not yield a silica fiber composition with sufficient flexibility for many applications, including for wound care or health care applications. Instead, these structures are comparatively brittle, rigid, and compact; mats will easily fracture or break; fiber layers are difficult to separate; and generally lack the physical characteristics to mimic collagen deposition in a wound. In various embodiments, to achieve a superior material for tissue repair, it is important to electrospin the sol-gel once it is appropriately ripened (or "transitioned"), to achieve a composition with the desired physical characteristics. By transitioning the sol under controlled environmental conditions, and/or monitoring the preparation of the sol-gel during the ripening process, the relatively short window to successfully electrospin the sol-gel can be identified. In accordance with embodiments of the invention, the composition is non-rigid and has a soft texture similar to that of cotton.

In accordance with embodiments of the invention, the silica fiber composition, when applied to wounded tissue, acts as a non-biodegradable scaffold that supports tissue healing, regeneration, and/or integrity. The composition acts as a collagen biomimetic at the site of tissue injury, providing an environment conducive for regeneration and growth of dermal cells. Without wishing to be bound by theory, the composition and methods described herein avoid the problem of temperature dysregulation as well as excess pain and inflammation at the wound site, allowing for the wound environment to normalize. Further, uncontrolled tissue degradation processes can destroy newly deposited collagen, which is needed to support tissue regeneration. The composition of the invention provides a non-biodegradable cell scaffold that is not destroyed by proteases released at the wound site, but provides an optimal environment for population and growth of dermal cells. The fibers will not be removed from the wound, but will become an integral part of the new tissue.

The fibers may have a variable diameter, such as in the range of from about 50 nm to 5 µm. In some embodiments, the fibers are predominately in the range of about 100 nm to about 2 µm, or predominately in the range of about 200 to about 800 nm. The variable size of the fibers can be a better mimic for natural collagen, compared to, for example, scaffolding intended to have a more uniform structure. The different cell types involved in tissue healing or regeneration require different size diameters of collagen. Without intending to be bound by theory, cells that migrate into the fibers have the ability to direct positioning of the fibers, as needed to support growth, adherence, or proliferation of the particular cell. Further, tissue requires a lot of surface area, which is provided by the fiber material. This is in contrast to many 3D printing and other synthetic scaffolding alternatives that lack substantial surface area. Further still, biodegradable scaffoldings, which have been conventionally preferred, typically degrade too quickly, before the tissue has the ability to grow and become self-sustainable.

For example, macrophages secrete a variety of cytokines and growth factors such as fibroblast growth factor (FGF), epidermal growth factor (EGF) and transforming growth factor beta that can stimulate keratinocytes, fibroblasts, and other cells required for angiogenesis, collagen deposition, granulation tissue formation, wound contraction and epithelialization. Fibroblasts secrete the collagen framework that allows for dermal regeneration. However, macrophages as well as epithelial cells and fibroblasts also secrete extracellular enzymes (e.g., matrix metalloproteinases, MMPs) at the site of the wound to degrade necrotic tissue and apoptotic cells. MMPs act on all components of the extracellular matrix and are responsible for removal of devitalized tissue, repair of lost or damaged tissue, and remodeling. MMPs are balanced by tissue inhibitors of metalloproteinases (TIMPs), which are released locally by cells to deactivate the MMPs. Uncontrolled activity of MMPs may result in degradation of newly formed tissue (including collagen) or destruction of growth factors, which will interfere with wound healing. By providing the non-biodegradable scaffold, uncontrolled activity of MMPs will not interfere with population and growth of dermal cells.

In some embodiments, the sol-gel for preparing the silica fiber composition is prepared by a method that includes preparing a first mixture containing an alcohol solvent, a silicon alkoxide reagent such as Tetraethyl ortho silicate (TEOS); preparing a second mixture containing an alcohol solvent, water, and an acid catalyst; fully titrating the second mixture into the first mixture; and processing (ripening) the combined mixture under controlled environmental conditions to form a gel for electrospinning.

In some embodiments, the silicon alkoxide reagent is TEOS. Alternative silicon alkoxide reagents include those with the formula Si(OR)4, where R is from 1 to 6, and preferably 1, 2, or 3

In some embodiments, the alcohol solvent is an anhydrous denatured ethanol, or in some embodiments, methanol, propanol, butanol or any other suitable alcohol solvent. The first mixture can be agitated, for example, using a magnetic stirrer or similar agitation means. The second mixture contains an alcohol solvent, water, and an acid catalyst. The alcohol solvent may be an anhydrous denatured alcohol, or may be methanol, propanol, butanol or any other suitably provided alcohol solvent. Water may be distilled water or deionized water. Enough acid catalyst is added to the mixture to aid in the reaction. This acid catalyst may be hydrochloric acid, or may be sulfuric acid or other suitable acid catalyst. The second mixture may be agitated, for example, with a magnetic stirrer or other agitation means. In some embodiments, the first mixture (or sol) and the second mixture (or sol) are created without the use of direct heat.

In some embodiments, the sol contains 70% to 90% tetraethyl orthosilicate (TEOS) by weight, 12% to 25% ethanol by weight, 1% to 10% water by weight, and an acid catalyst. In some embodiments, the sol contains 75% to 85% by weight TEOS, 15% to 20% by weight ethanol, and about 2% to 5% by weight water. An exemplary sol contains about 80% by weight TEOS, about 17% by weight ethanol, and about 3% by weight water. In some embodiments, the acid catalyst is HCl. For example, the sol may contain less than about 0.1% HCl by weight. For example, the sol may contain from 0.02% to 0.08% HCl by weight. In various embodiments, the sol does not contain an organic polymer, or other substantial reagents, such that the fiber composition will be substantially pure SiO2. In various embodiments, the fiber composition does not include metals or metal oxides (e.g., TiO2 or ZrO2).

According to various embodiments, the first mixture and the second mixture are combined by dripping or titrating the second mixture into the first mixture, preferably with agitation. The combined mixture is then further processed by allowing the sol to ripen in a controlled environment until a substantial portion of the alcohol solvent has evaporated to create a sol-gel suitable for electrospinning In various embodiments, the sol is not exposed to heat over 150° F. or heat over 100° F., so as to avoid accelerating the transition.

In exemplary embodiments of the invention, the controlled environment may include an enclosure with at least one vent and optionally an exhaust fan to draw gases away from the mixture. The enclosure may involve controlled conditions in terms of humidity, temperature, and optionally barometric pressure. For example, the humidity may be controlled (e.g., via use of conventional humidifiers and/or dehumidifiers) within the range of about 30% to about 90%, such as from about 40% to about 80%, or in some embodiments, from about 50% to about 80%, or from about 50% to about 70% (e.g., about 55%, or about 60%, or about 65%). Some humidity can be helpful to slow evaporation of solvent, and thereby lengthen the window for successful electrospinning. In some embodiments, the temperature is in the range of from about 50° F. to about 90° F., such as from about 60° F. to about 80° F., or from about 65° F. to about 75° F. In some embodiments, barometric pressure is optionally controlled (e.g., using a low pressure vacuum source). By controlling the environmental conditions during ripening, the gel can be electrospun during the time when spinning is optimal, which can occur in a small window of only several minutes if the ripening process is too accelerated, such as with direct heat. When ripening the sol at a constant humidity of about 55% and temperature of about 72° F., the sol will ripen (gelatinize) in a few days, and the window for successful electrospinning can be expanded to at least several hours, and in some embodiments several days. In various embodiments, the ripening process takes at least 2 days, or at least 3 days in some embodiments. However, in various embodiments the ripening does not take more than 10 days, or more than 7 days. In some embodiments, the ripening process takes from 2 to 7 days or from 2 to 5 days or from 2 to 4 days (e.g., about 2, about 3, or about 4 days). In various embodiments, the sol-gel is spinnable well before it transitions into a more solidified, non-flowable mass.

The enclosure space for ripening the sol-gel may include a vent on at least one surface for exhausting gases from within the enclosure, and optionally the vent may include a fan for exhausting gases produced during the ripening process. The enclosure space may optionally include a heating source for providing a nominal amount of heat within the enclosure space, to maintain a preferred temperature. In some embodiments, a source of humidity is provided within the enclosure environment to adjust the humidity to a desired range or value. The enclosure may further include one or more environmental monitors, such as a temperature reading device and/or a humidity reading device.

In some embodiments, the sol-gel is electrospun after a ripening process of at least 2 days, or at least 36 hours, or at least 3 days, or at least 4 days, or at least 5 days at the controlled environmental conditions (but in various embodiments, not more than 10 days or not more than 7 days under the controlled environmental conditions). By slowing the ripening process, the ideal time to spin the fibers can be identified. The weight of the sol-gel can be used as an indicator of when the sol-gel is at or near the ideal time to electrospin. Without intending to be bound by theory, it is believed that the viscosity of the sol-gel is a poor determinant for identifying the optimal time for electrospinning. For example, in various embodiments, the sol-gel is from about 10% to about 60% of the original weight of the sol (based on loss of alcohol solvent during transitioning). In some embodiments, the sol-gel is from 15 to 50% of the original weight of the sol, or in the range of about 20 to about 40% of the original weight of the sol.

In some embodiments, the sol-gel is ripened for at least 2 days, or at least 36 hours, or at least 3 days, or at least 4 days, or at least 5 days, and is electrospun when the ethylene vapors produced by the composition are between about 10% and about 40% of the vapors produced by the starting sol, such as in the range of about 10% and about 25%, such as in the range of about 10 to about 20%. Ethylene is a colorless flammable gas with a faint sweet and musky odor (which is clearly evident as solvent evaporation slows). Ethylene is produced by the reaction of ethanol and acid. Ethylene can optionally be monitored in the vapors using a conventional ethylene monitor. In other embodiments, gases produced by the sol during the sol ripening process are monitored to determine the suitable or optimal time for electrospinning. Gas profiles can be monitored using gas chromatography.

The processing of the sol-gel mixture may require stirring or other agitation of the mixtures at various intervals or continuously due to the development of silicone dioxide crystalline material on the top surface of the mixtures. This development of crystalline material on the top surface slows the processing time and it is believed that the crystalline material seals off exposure of the mixture to the gaseous vacuum provided within the enclosure space. In some embodiments, any solid crystalline material is removed from the mixture.

Upon completion of the sol-gel process, the sol-gel is then electrospun using any known technique. The sol or sol-gel may be preserved (e.g., frozen or refrigerated) if needed (and such time generally will not apply to the time for ripening). An exemplary process for electrospinning the sol-gel is described in Choi, Sung-Seen, et al., *Silica nanofibers from electrospinning/sol-gel process, Journal of Materials Science Letters* 22, 2003, 891-893, which is hereby incorporated by reference in its entirety. Exemplary processes for electrospinning are further disclosed in U.S. Pat. No. 8,088,965, which is hereby incorporated by reference in its entirety.

In an exemplary electrospinning technique, the sol-gel is placed into one or more syringe pumps that are fluidly coupled to one or more spinnerets. The spinnerets are connected to a high-voltage (e.g., 5 kV to 50 kV) source and are external to and face toward a grounded collector drum. The drum rotates during spinning, typically along an axis of rotation approximately perpendicular to the spinning direction extending from the spinnerets to the drum. As the sol-gel is supplied to the spinnerets from the syringe pumps (or other holding tank), the high voltage between the spinnerets and the drum forms charged liquid jets that are deposited on the drum as small entangled fibers. As the drum rotates and electrospinning continues, a fibrous mat of silica fibers is formed around the circumference of the drum. In various embodiments, the spinnerets and syringe pump(s) may be disposed on a movable platform that is movable parallel to the length of the drum. In this manner, the length along the drum of the resulting fiber mat may be increased without increasing the number of spinnerets. The diameter of the drum may also be increased to increase the areal size of the electrospun mat. The thickness of the mat may be largely dependent upon the amount of sol-gel used for spinning and thus the amount of electrospinning time. For example, the mat may have a thickness of greater than about ⅛ inch, or greater than about ¼ inch, or greater than about ⅓ inch, or greater than about ½ inch.

Silica fiber mats and compositions produced in accordance with embodiments of the present invention exhibit one or more beneficial properties when compared to fiber compositions spun at non-optimal times (e.g., with inadequate ripening of the sol-gel). For example, fiber mats and compositions in accordance with embodiments of the invention do not burn, char, or visibly degrade upon direct application of heat or open flame. In contrast, various fiber compositions spun at non-optimal times will exhibit charring and/or visible color change when exposed to sufficient heat or open flame. Moreover, fiber mats and compositions in accordance with embodiments of the invention effectively wick moisture (e.g., water or bodily fluids), absorbing such fluid into the fiber mat. In contrast, various fiber compositions spun at non-optimal times will not visibly absorb or wick moisture even when directly applied thereto; such compositions tend to be hydrophobic. Finally, fiber mats and compositions in accordance with embodiments of the invention are fluffy and may be easily shaped to uneven, non-uniform, and/or non-planar (e.g., curved) surfaces or shapes without fracturing or loss of structural integrity; thus, such compositions may be readily applied to or conformed to a variety of different surfaces. In contrast, various fiber compositions spun at non-optimal times tend to be flat, plate-like, brittle, and will at least partially fracture if excessively mechanically shaped or bent.

Fiber layers can be easily separated from the mat for, e.g., application to wounds or to damaged or inflamed tissue. In some embodiments, the composition is electrospun with a thickness of from about ⅛ inch to about ½ inch. For example, the composition may be electrospun with a thickness of greater than about ⅛ inch, or greater than about ¼ inch thick, or about ¼ thick in some embodiments.

In some embodiments, the fiber composition is applied to the tissue or wound as a thin layer of fibers, e.g., just enough to cover the wound surface. Often, the wound will quickly absorb the fibers. The process is repeated once fibers are no longer visible on the wound. For example, in some embodiments, fibers are reapplied 2 to 5 times per day. In some embodiments, the fiber composition is processed into a fine powder or dust, and the powder or dust is applied to the tissue. For example, a sheet of silica fibers can be rubbed through one or more screens, and a range of powder sizes obtainable by varying mesh size. In some embodiments, the powder or dust is mixed with a topical composition, such as a lotion, ointment, paste, cream, foam, or gel. In these embodiments, the topical composition may comprise one or more pharmaceutical or antimicrobial agents, such as an antibiotic, an antiseptic, an anti-inflammatory agent, or immunosuppressant.

Application of the composition during the healing process can provide for accelerated healing, of both acute and chronic wounds, and can prevent or reduce tissue scarring. When the topical composition is applied to the skin that has a blemish like acne, cracks in skin, small scrapes etc., the scaffolding is left behind in the small wound for cells to grow into. This speeds up the healing process and helps to reduce scarring. In some embodiments, the composition in lotion form is applied to the cracked skin (e.g., on the face or hands) to improve tolerance of the skin to the environment, such as sun, wind, and cold, thereby reducing the impact of age and environment on the appearance and/or function of the skin.

In some embodiments, the subject is a mammal. Subjects include veterinary patients such as a dog, cat, or horse, among others. In some embodiments, the patient is a human patient. The tissue can be of any organ, but in some embodiments comprises skin, muscle, or bone. In some embodiments, the composition is applied to a skin lesion, ulcer, wound, burn, cut, scrape, or blister.

In some embodiments, particularly for chronic or difficult to heal wounds, the fiber scaffold normalizes the wound environment, including temperature dysregulation, may reduce pain and inflammation at the wound site, and/or provides a scaffold for dermal cells to multiply and grow into (e.g., without full, natural deposition of collagen).

In some embodiments, the wound is a burn, scrape, or cut, or a minor wound that does not go deeper than the base lamina. In such embodiments, treatment with the fiber scaffold for 1 to 7 days, e.g., from 3 to 5 days (about 4 days) is sufficient for substantially complete healing. In such embodiments, fibers are applied once to four times daily to cover the wound. Fibers are generally reapplied when fibers are no longer visible in the wound.

In some embodiments, the wound includes damage including or past the base lamina. Such wounds may require treatment for several weeks (e.g., from 2 to 8 weeks), or in some embodiments, several months (e.g., from 1 to 4 months) for very severe wounds. In some embodiments, the wound is a diabetic ulcer, chronic pressure sore, gangrenous wound, or amputation wound. For difficult or hard to treat wounds, such as gangrenous wounds or wounds with substantial necrotic tissue (e.g., necrotizing fasciitis), the fiber compositions may mimic the healing process, and induce gene expression and/or environment conducive to healing. Further, application of the fibers will bypass the need for deposition of natural collagen during the uncontrolled inflammatory state. Further, bacteria at the wound site cannot easily penetrate the fiber to get to the wound. In these embodiments, fibers are applied once to four times daily to cover the wound. Fibers are generally reapplied when fibers are no longer visible in the wound. A wound cover can by employed where necessary, as long as air and oxygen is not restricted from the wound.

In some embodiments, because the fiber material substantially reduces pain from the wound site, the patient may be able to forgo therapy with a pain medication such as an opioid.

In some embodiments, the fibers may be applied to a rash or other manifestation of skin inflammation (e.g., shingles, or an autoimmune rash or lesion, or allergic rash), resulting in reduction in pain and/or inflammation. In some embodiments, the fibers are applied with a gel or cream or other topical composition to mediate adherence of fibers to substantially intact skin.

In some embodiments, the subject has a genetic blistering disease, such as epidermolysis bullosa. Epidermolysis bullosa (EB) is a group of mainly inherited connective tissue diseases that cause blisters in the skin and mucosal membranes. It is a result of a defect in anchoring between the epidermis and dermis, resulting in friction and skin fragility. Epidermolysis bullosa often involves formation of blisters following trivial trauma.

In some embodiments, the subject has Epidermolysis bullosa simplex, which results in blisters at the site of rubbing, and typically affects the hands and feet. In some embodiments, the subject has Junctional epidermolysis bullosa, which affects laminin and collagen. Junctional epidermolysis bullosa also presents with blisters at the site of friction, especially on the hands and feet. Dystrophic epidermolysis bullosa is an inherited variant affecting the skin and other organs, and involves skin that is very fragile. Dystrophic epidermolysis bullosa is caused by genetic defects (or mutations) within the gene encoding the protein type VII collagen (collagen VII).

The human skin consists of two layers: an outermost layer called the epidermis and a layer underneath called the dermis. In individuals with healthy skin, there are protein anchors between these two layers that prevent them from moving independently from one another (shearing). In people born with EB, the two skin layers lack the protein anchors that hold them together, resulting in extremely fragile skin. Even minor mechanical friction (like rubbing or pressure) or trauma will separate the layers of the skin and form blisters and painful sores. Sufferers of EB have compared the sores with third-degree burns.

In some embodiments, when the fiber composition is applied to EB blisters, sores, wounds, or lesions, the composition will become integrated with the healing tissue including the base lamina in some embodiments, and help anchor the skin. Thus, over time, the skin exhibits improved integrity as sores and blisters are treated. Further, the reduction in pain can be important for these patients to perform daily activities, such as bathing or traveling.

The thickness of fiber that is applied to the wound depends on the depth of the wound, but generally just enough fibers are applied to cover the wound. The composition may be reapplied after fibers are no longer visible at the wound site. The composition may also be freshly reapplied after bathing. It is believed, without wishing to be bound by theory, that the fibers become integrated with the regenerated tissue at the wound site.

While the wound in some embodiments is not covered with any other wound dressing, in some embodiments other wound dressings can be employed. For example, in some embodiments the wound is not covered (other than the fiber composition), allowing exposure of air and therefore sufficient availability of oxygen. However, for more severe wounds a dressing may be needed. Preferably, the dressing is a light covering that will not limit oxygen to the site. The fibers will not be removed. Since they are not biodegradable, they will become part of the new tissue. For shallow wounds, the scaffold is likely shed along with the skin tissue that integrates with it.

In some embodiments, the wound is a skin cancer lesion, such as a melanoma or squamous cell carcinoma (SCC) or basal cell carcinoma (BCC) lesion or ulcer. By application of the fibers to the lesion, the outgrowth of malignant cells (including cancer stem cells) is prevented or reduced, while normal cells are able to grow in the fiber network. Without wishing to be bound by theory, it is believed that the cancer cell phenotype is less able to populate the fiber matrix than normal cells. Further, cancers may rely on their ability to degrade collagen to grow, such that cancer cells are restricted from growing by their inability to degrade the fiber scaffold.

In other applications, fiber compositions in accordance with embodiments of the present invention may be added to various other compositions to improve one or more mechanical and/or thermal properties thereof, as detailed in U.S. Provisional Patent No. 62/643,946 filed Mar. 16, 2018, the entire disclosure of which is incorporated by reference herein. Specifically, entire silica fiber mats, or sections thereof may be utilized. In other embodiments, a silica fiber mat or portion thereof may be broken into a plurality of fragments, or even into a powder, for use as a beneficial additive with a (typically liquid or gelatinous) composition in order to impart advantageous thermal and/or mechanical properties thereto. For example, the fiber composition may be incorporated within paints or other coatings (e.g., adhesives, epoxies, etc.) in order to increase the thermal resistance per unit area (i.e., the "R-value") of the composition once it is applied. In other embodiments, the fiber composition is added to structural compositions, such as epoxies or urethanes, in order to increase the mechanical strength and/or impact resistance of the material once it is formed (e.g., molded) into a solid object. The fiber composition may also be mixed into a liquid, which may subsequently be applied to articles such as fabrics to impart beneficial characteristics thereto. The liquid composition in such embodiments may dry onto the article and become a portion thereof or a layer thereon. For example, silica fiber-containing compositions may be applied to clothing to impart fire resistance or impact resistance thereto in the manner of a fire-resistant suit or an armored or bullet-proof vest.

Embodiments of the invention will now be described with respect to the following examples.

EXAMPLES

Example 1: Preparation of Silica Fiber Composition

SiO2 fibers were prepared using an electrical spinning process, where a sol-gel is spun onto a roller system creating a sheet. The sol-gel is made in two parts. First, TEOS (tetraethyl orthosilicate) is mixed with ethanol, and then a second mixture containing HCl, water, and ethanol is titrated into the mixture. The sol-gel is then allowed to ripen for a few days under controlled conditions before spinning.

In one example, the first sol was made by weighing out 384 grams of (TEOS) Tetraethyl orthosilicate 98% and 41.8 grams of Anhydrous Denatured Ethanol, and pouring together. The first sol was allowed to let stand in a beaker and a magnetic stirrer was used to create a homogenous solution. The second sol was made by weighing 41.8 grams of Anhydrous Denatured Ethanol, 16.4 grams of Distilled water, and 0.34 grams of Hydrochloric Acid, which was then poured together and mixed for 8 seconds with a magnetic stirrer until a homogenous second sol was formed.

The second sol was then poured into the titration device, which was placed above a beaker containing the first sol. The titration device then dripped about 5 drops per second until a third sol was formed mixing the first sol and the second sol. During the dripping process, the first sol continues to be mixed with a magnetic stirrer while the second sol is dripped into the first sol.

The combined third sol was then placed into an enclosure box. A low pressure vacuum is provided by a fan on medium speed to remove fumes. In the experiment, the air temperature within the box was 72° F. with 60% humidity. In the experiment, the third sol was allowed to sit and process for about three (3) days. By ripening the sol-gel slowly over several days, the sol-gel will transition slowly such that the ideal time to electrospin can be identified.

The mixtures were agitated daily to reduce the build-up of crystalline structures. The third sol begins to transition to sol-gel with evaporation of the alcohol solvent. Sol-gel may be monitored to determine an approximate amount of C2H4 (ethylene) in the vapors, which can be in the range of about 10-20% relative to the original sol before ripening. Upon proper gelatinization, the sol-gel is loaded into the electrospinning machine or is frozen to preserve for electrospinning. Proper gelatinization occurs when the total mass of the sol-gel was between about 100 grams and about 180 grams The above example can be scaled appropriately to produce desirable structures. To further identify the ideal time to electropsin, portions of the gel can be dripped into the electric field to evaluate the properties of the resulting fibers.

FIGS. 1A-D shows Scanning Electron Microscopy (SEM) images of fibers spun in accordance with this disclosure (50, 100, 200, and 500 micron scales shown). As shown, the fibers are flexible, smooth, dense, and continuous (not fractured). Material with these properties is ideal for treating wounds and animal tissues (e.g., as a collagen mimetic)

Figure 3:
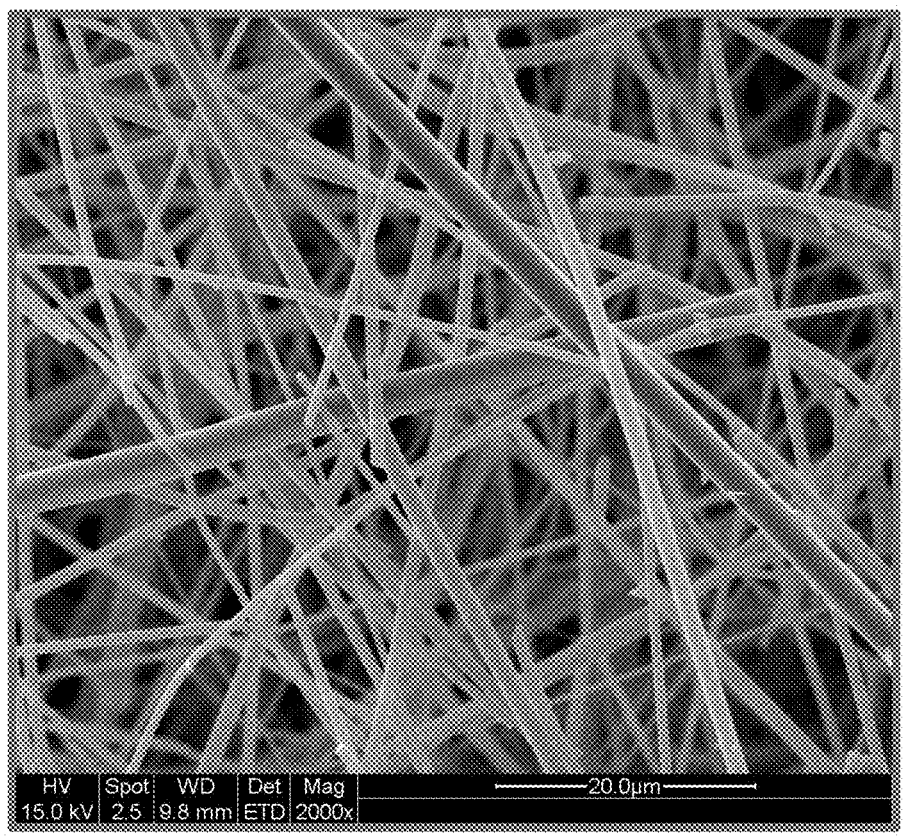
FIG. 3 shows an SEM image (20 micron scale is shown) of fibers spun at a non-optimal time. The fibers are rigid, with fractures clearly evident.

FIGS. 2A-D shows Scanning Electron Microscopy (SEM) images of fibers that were electrospun at a non-optimal time (before the sol-gel was fully ripened) (50, 100, 200, and 500 micron scale shown). The fibers appear rigid, with many fractures visible, and with formation of clumps. FIG. 3 shows an SEM image (20 micron scale is shown) of fibers from a similar material, where the fibers are clearly rigid with many fractures clearly evident.

Figure 4:
FIG. 4 shows a fiber mat spun with a thickness of about ¼ inch in accordance with the disclosure. The mat has a soft, flexible texture FIGS. 5A-B compares a silica fiber mat that was electrospun when the sol-gel was transitioned in accordance with this disclosure, FIG. 5A, as compared to a fiber mat that was spun too early, before the sol-gel was optimally ripened, FIG. 5B. The material in the FIG. 5A has a soft texture, is very flexible, and can be spun at a thickness that is easily handled for application of fiber layers to a wound. The material in FIG. 5B is brittle, inflexible, and layers of fiber cannot be easily separated for covering the surface area of a wound.
Figure 5A:
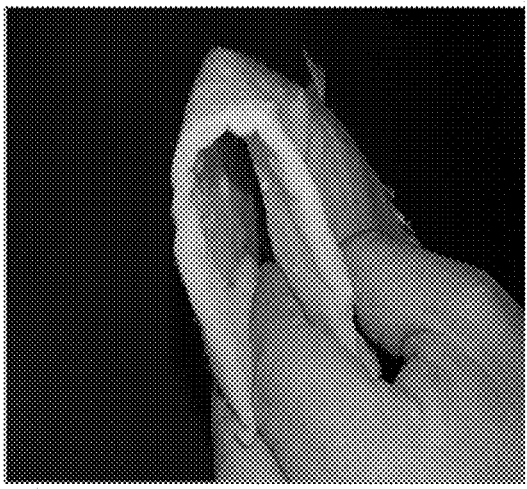
Figure 5B:
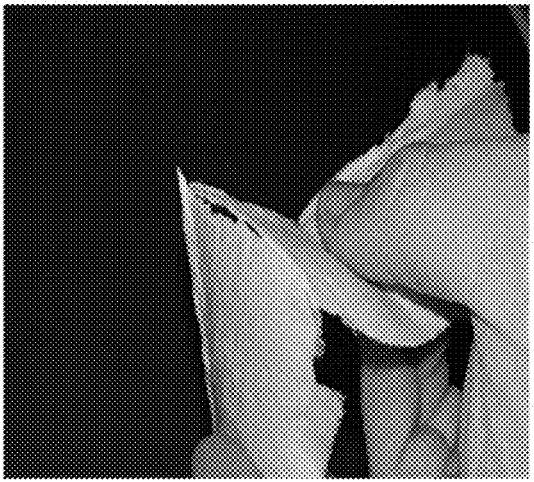

FIG. 4 shows a fiber mat spun in accordance with the disclosure. The flexibility and continuity of the fibers allows mats to be spun at a thickness of ¼ inch or more. The mat has a soft, flexible texture, and allows for layers of fibers to be easily separated for covering a wound bed. FIG. 5A-B, respectively compares a silica fiber mat that was electrospun when the sol-gel was ripened in accordance with this disclosure FIG. 5A, as compared to a fiber mat that was spun too early, before the sol-gel was optimally ripened FIG. 5B.

The 19 material in FIG. 5A has a soft texture, is very flexible, and can be spun at a thickness that is easily handled for application of fiber layers to a wound. The material on the right is brittle, inflexible, thin, and layers of fiber cannot be easily separated for covering the surface area of a wound.

Example 2: Treatment of Burn

Fibers were applied to first and second degree burns to the face of an adult male. The amount applied was just enough to cover the wound sites, with the thickness of the fibers based on the depth of the wound. After initial application of the fibers, additional fibers were added once fibers were no longer visible. After 4 days burns were barely visible.

Figure 6:
FIG. 6 shows application of a thin section of fiber to a burn wound
Figure 7B:
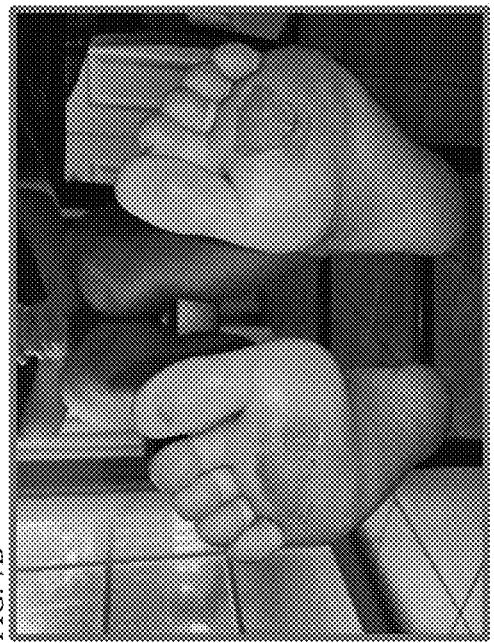
FIG. 7B shows the same wound after 4 days of treatment with the fiber scaffold.
Figure 7D:
FIG. 7D shows the same wound after 12 days of treatment with the fiber scaffold.
Figure 7A:
FIG. 7A is picture of a burn before application of fibers.
Figure 7C:
FIG. 7C shows the same wound after 8 days of treatment with the fiber scaffold.

Fibers were applied to second degree burns to the arm of an adult male. Application of thin sections of material to the burn wound is shown in FIG. 6.

Fibers were applied to 2nd degree burns on the feet of an adult woman, with substantial healing shown in a four-day period. After initial application of the fibers, additional fibers were added once fibers were no longer visible. Fibers were also reapplied after bathing. A picture of the burns pretreatment and pictures taken in 4-day intervals (during treatment) are shown in FIGS. 7A, 7B, 7C, and 7D.

Example 3: Treatment of Amputation Wound

The fiber scaffolding was applied to a gangrenous wound site where the toe had been amputated. The wound was a diabetic wound, which are extremely hard to heal, and difficult to stop the necrotic processes.

The wound healed in about 5 to 6 weeks with application of the fiber matrix. Prior to treatment, the foot was at risk of needing amputation. However, after treatment with the fibers, the foot was ultimately saved.

Example 4: Treatment of Animal Wounds

Figure 8B:
FIG. 8B shows the wound after about 3 months of treatment.
Figure 8A:
FIG. 8A is a picture of a dog leg wound with fiber graft.

The fiber scaffolding was applied to a deep wound on a dog's leg, which was recommended for amputation. After treatment for 2-3 weeks, the wound was fully healed, and a full covering of fur developed over the wound within 3 months. Pictures of the wound with fiber graft are shown (FIG. 8A), and again after about 3 months of treatment (FIG. 8B).

Figure 9C:
FIG. 9C shows the wound fully healed.
Figure 9B:
FIG. 9A is a picture of a wound on a horse leg. The wound after treatment with fibers for about 4 days is shown in FIG. 9B.
Figure 9A:

The fiber scaffolding was applied to a deep wound on a horse's leg, which was ripped open by a fence. The wound was causing the horse to limp badly. Wounds on horses are very hard to heal, especially wounds on their legs. The fibers were applied at night while the horse was in the barn (FIG. 9A). The next morning the horse was trotting limp free, suggesting that the horse no longer had the same pain sensations from the wound site. The same wound is shown after 4 days of treatment in FIG. 9B. That wound is now fully healed (FIG. 9C).

Example 5: Treatment of Pressure Sores

A paraplegic adult male with a severe bed sore on his lower back was treated with the fibers. The wound was a chronic wound that existed for at least 17 months. When a paralyzed person has a wound, instead of feeling pain, they tend to sweat profusely. When the fibers were added to the wound, the subject stopped sweating. After treatment for several months the wound is nearly healed.

Example 6: Treatment of Epidermolysis Bullosa (EB) Wounds

Figure 10B:
FIG. 10B shows the same hand after healing.
Figure 10A:
FIG. 10A is a photograph of a child with Epidermolysis Bullosa (EB), with a graft of the fibers applied to a large open wound on the hand.

A child with Epidermolysis Bullosa (EB) was treated by applying the fibers to open sores and blisters. Application of the fibers allowed the child to take a bath without pain, eliminating the need for pain drugs during bath time. Application of the fibers to a severe open wound on the child's hand is shown in FIG. 10A. The same hand after healing is shown in FIG. 10B. When a rub test (to induce a blister) is conducted on the healed site with the fibers, the skin does not blister.

The invention claimed is:

1. A method for making a silica fiber composition, comprising:
   preparing a sol that contains 70% to 90% tetraethyl orthosilicate (TEOS) by weight, 12% to 25% ethanol by weight, 1% to 10% water by weight, and an acid catalyst;
   transitioning the sol to a sol-gel for 2 to 7 days under conditions where humidity is within the range of 40% to 80%, and the temperature is within the range of 50 to 90° F.; and
   electrospinning the sol-gel into a silica fiber mat.
2. The method of claim 1, wherein the sol is not exposed to heat over 150° F.
3. The method of claim 2, wherein the sol is not exposed to heat over 100° F.
4. The method of claim 1, wherein the sol contains 75% to 85% by weight TEOS, 15% to 20% by weight ethanol, and about 2% to 5% by weight water.
5. The method of claim 4, wherein the sol contains about 80% by weight TEOS, about 17% by weight ethanol, and about 3% by weight water.
6. The method of claim 1, wherein the acid catalyst is HCl.
7. The method of claim 6, wherein the sol contains less than about 0.1% HCl by weight.
8. The method of claim 7, wherein the sol contains from 0.02% to 0.08% HCl by weight.
9. The method of claim 1, wherein the sol does not contain an organic polymer.
10. The method of claim 1, wherein the sol is allowed to transition for 2 to 4 days.
11. The method of claim 10, wherein the sol is allowed to transition for about 3 days.
12. The method of claim 1, wherein the humidity is 50 to 70%.
13. The method of claim 12, wherein the temperature is 60 to 80° F.
14. The method of claim 1, wherein the conditions further comprise a fan exhausting gases from the sol.
15. The method of claim 1, wherein the sol-gel is electrospun when the weight is at from 20% to 40% of the starting weight of the sol.
16. The method of claim 1, wherein the sol-gel is electrospun when the production of ethylene vapor is 10% to 20% relative to the peak production of ethylene vapors from the sol.
17. The method of claim 1, wherein the mat has a thickness of at least about ⅛ inch.
18. The method of claim 17, wherein the mat has a thickness of at least about ¼ inch.
19. A method for making and using a silica fiber composition, the method comprising:

preparing a sol that contains 70% to 90% tetraethyl orthosilicate (TEOS) by weight, 12% to 25% ethanol by weight, 1% to 10% water by weight, and an acid catalyst;

transitioning the sol to a sol-gel for 2 to 7 days under conditions where humidity is within the range of 40% to 80%, and the temperature is within the range of 50 to 90° F.;

electrospinning the sol-gel into a silica fiber mat; and applying at least a portion of the silica fiber mat to injured tissue of a subject, the subject being a human or veterinary patient.

20. The method of claim 19, wherein, during and after healing of the injured tissue, at least some of the silica fiber mat is not removed from the tissue.

21. The method of claim 19, wherein at least a portion of the silica fiber mat is processed into a powder or dust.

22. The method of claim 21, wherein the powder or dust are mixed or suspended with a topical composition, the topical composition being a lotion, ointment, paste, cream, foam, or gel.

23. The method of claim 22, wherein the topical composition further comprises one or more pharmaceutical or antimicrobial agents.

24. The method of claim 23, wherein the topical composition comprises an antibiotic, an antiseptic, an anti-inflammatory agent, or an immunosuppressant.

25. A method for making and using a silica fiber composition, the method comprising:

preparing a sol that contains 70% to 90% tetraethyl orthosilicate (TEOS) by weight, 12% to 25% ethanol by weight, 1% to 10% water by weight, and an acid catalyst;

transitioning the sol to a sol-gel for 2 to 7 days under conditions where humidity is within the range of 40% to 80%, and the temperature is within the range of 50 to 90° F.;

electrospinning the sol-gel into a silica fiber mat; and combining at least a portion of the silica fiber mat with a liquid or gelatinous composition.

26. The method of claim 25, wherein the liquid or gelatinous composition comprises a paint, an epoxy, a urethane, or an adhesive.

27. The method of claim 25, wherein the at least a portion of the silica fiber mat is processed into a plurality of fragments or a powder for combination with the liquid or gelatinous composition, whereby a modified composition is formed.

28. The method of claim 27, further comprising applying the modified composition as a coating to a solid object or a fabric.

29. The method of claim 27, further comprising molding the modified composition into a solid object.

* * * * *